US00PP29341P3

(12) United States Plant Patent
Danziger

(10) Patent No.: US PP29,341 P3
(45) Date of Patent: May 29, 2018

(54) ***PETUNIA* PLANT NAMED 'DLITRDFIRE'**

(50) Latin Name: *Petunia hybrida*
Varietal Denomination: DLITRDFIRE

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 0 days. days.

(21) Appl. No.: 15/330,421

(22) Filed: Sep. 19, 2016

(65) Prior Publication Data

US 2018/0084696 P1 Mar. 22, 2018

(51) Int. Cl.
*A01H 5/02* (2018.01)

(52) U.S. Cl.
USPC ..... Plt./356.23
CPC ..... *A01H 5/02* (2013.01)

(58) Field of Classification Search
USPC ..... Plt./356.23
CPC ..... A01H 5/02
See application file for complete search history.

(56) References Cited

PUBLICATIONS http://nova.co.at/marsNova/en/instance/picture/Petunia-Littletunia-a-Red-Fire.xhtml?oid=9595605; Aug. 12, 2016; 2 pages.*

* cited by examiner

*Primary Examiner* — Kent L Bell
(74) *Attorney, Agent, or Firm* — Cassandra Bright

(57) ABSTRACT

A new and distinct *Petunia* cultivar named 'DLITRDFIRE' is disclosed, characterized by abundant flowering of small, red flowers and a mounded, ball-shaped habit that is very branched and has medium vigor. The new variety is a *Petunia*, suitable as an outdoor garden or container plant.

2 Drawing Sheets

Figure 1:
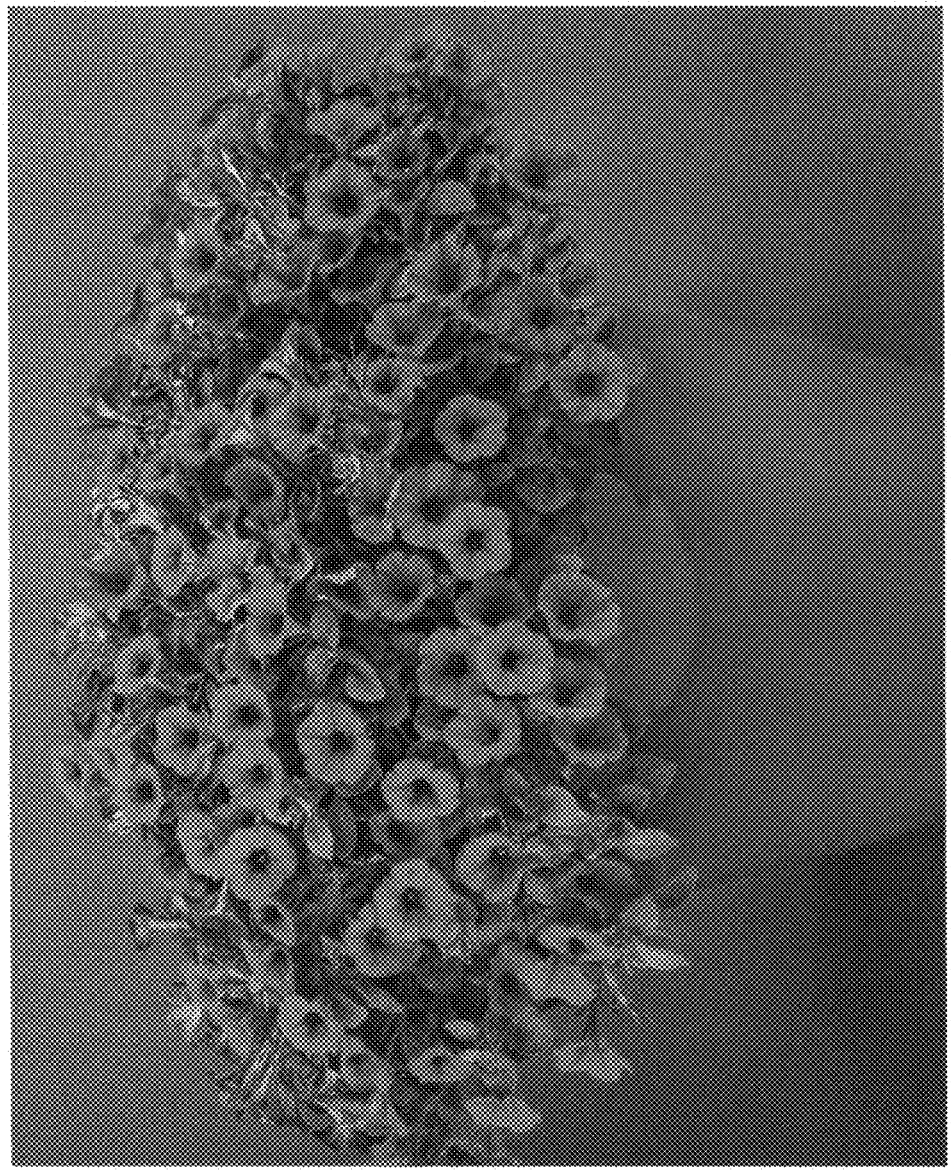

Latin name of the genus and species: *Petunia hybrida.*

Variety denomination: 'DLITRDFIRE'.

The new *Petunia* cultivar resulted as part of a planned breeding program by the inventor Gavriel Danziger. The objective of the breeding program was to develop new *Petunia* varieties with interesting colors and attractive plant forms.

The new variety resulted from the open pollination of the seed parent, an unpatented, proprietary seedling referred to as 'c.v. 12-6504' in May 2013. The new variety was discovered in November of 2013 by the inventor in a group of seedlings resulting from that open pollination in a research greenhouse in Moshav Mishmar Hashiva, Israel.

Asexual reproduction of the new cultivar 'DLITRDFIRE' by vegetative cuttings was first performed at a greenhouse as well as outdoors in Moshav Mishmar Hashiva, Israel in November of 2013. Subsequent propagation by vegetative cuttings has shown that the unique features of this cultivar are stable and reproduced true to type in more than 25 successive generations.

SUMMARY OF THE INVENTION

The cultivar 'DLITRDFIRE' has not observed under all possible environmental conditions. The phenotype may vary somewhat with variations in environment such as temperature, day length and light intensity, without however, any variance in genotype.

The following traits have been repeatedly observed and are determined to be the unique characteristics of 'DLITRDFIRE'. These characteristics in combination distinguish 'DLITRDFIRE' as a new and distinct *Petunia* cultivar:

1. Mounded, ball-shaped plant.
2. Very well branched plant with medium vigor.
3. Red flowers.
4. Small flowers.
5. Abundant flowering.

COMPARISON TO THE PARENT VARIETY

Plants of the new cultivar are similar to plants of the seed parent, in most horticultural characteristics, however, plants of the new cultivar differ in the following;

1. Parent is semi-upright whereas new variety is mounded.
2. Parent is compact and not very well branched whereas the new variety is very well branched.
3. Parent has medium flowers whereas the new variety has small flowers.
4. Parent has medium quantity of flowering whereas the new variety has abundant flowering.

COMPARISON TO COMMERCIAL VARIETIES

Plants of the new cultivar can be compared to the patented commercial variety *Petunia* 'Danlittun3' U.S. Plant Pat. No. 20,054. These varieties are similar in most horticultural characteristics; however, the new cultivar differs in the following:

1. Commercial comparator has dark pink flowers, whereas the new variety has red flowers.
2. Commercial comparator has low height whereas the new variety is of medium height.
3. Flower throat of commercial comparator is white, whereas the flower throats of the new variety is white with brown veins.

Plants of the new cultivar can be compared to the patented commercial variety *Petunia* 'Dantun2', unpatented. These varieties are similar in most horticultural characteristics; however, the new cultivar differs in the following:

1. Commercial comparator has smaller flowers than the new variety.
2. Commercial comparator has light pink flowers with dark purple veins whereas the new variety has red flowers.
3. Flower throat of commercial comparator is white, whereas the flower throats of the new variety is white with brown veins.

BRIEF DESCRIPTION OF THE PHOTOGRAPHS

The accompanying photograph in FIG. 1 illustrates in full color a typical plant of 'DLITRDFIRE' grown in a greenhouse, in a 10 inch commercial basket. Age of the plant photographed is approximately 20 weeks from 5 rooted cuttings.

Figure 2:
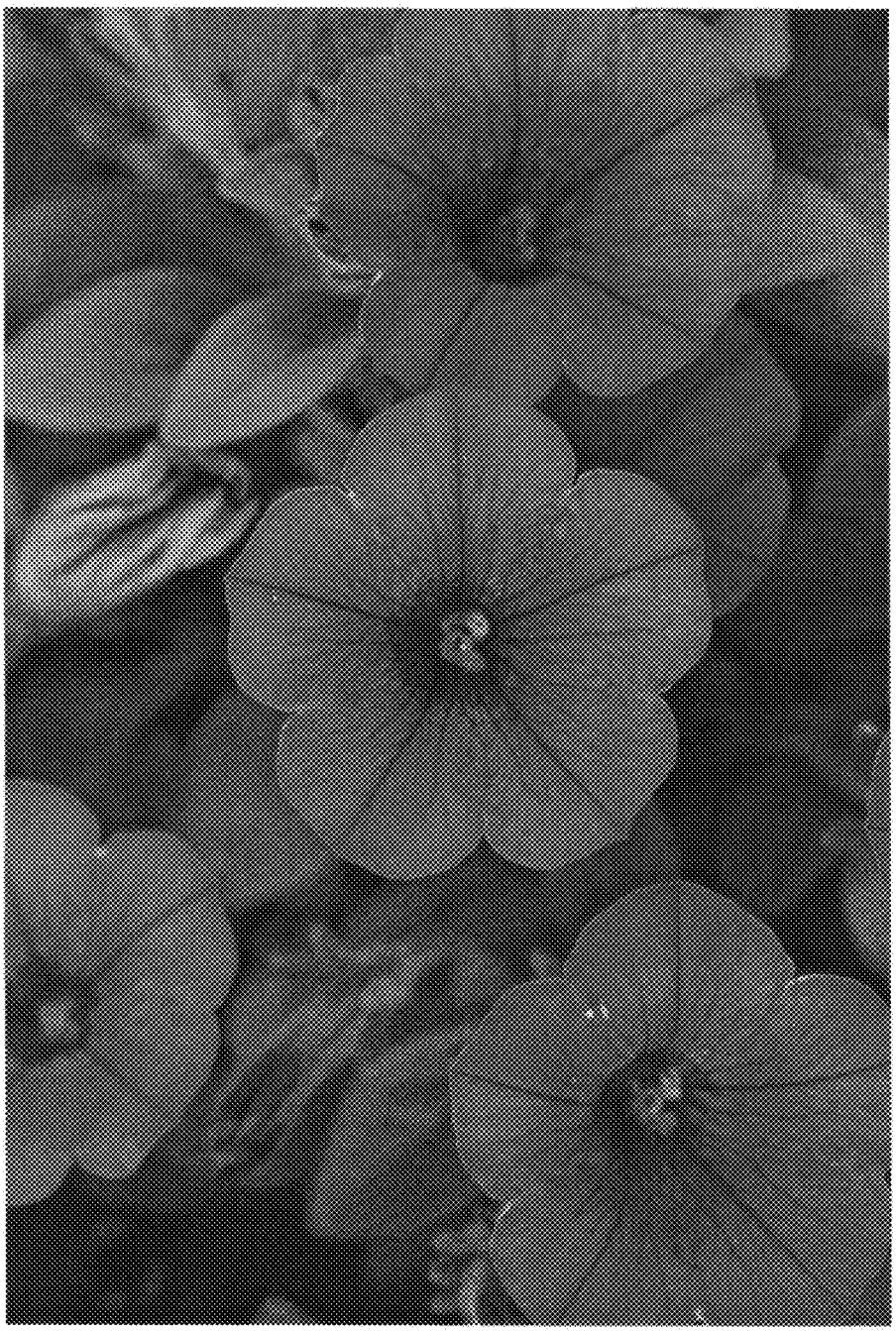

FIG. 2 illustrates a close up view of the flowers.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurement describe 'DLITRDFIRE' plants grown in a greenhouse and outdoors in Moshav Mishmar Harshiva, Israel during the spring, summer, and autumn. The growing temperature ranged from 20° C. to 35° C. General light conditions are bright, normal sunlight with some shade during the brightest part of the day. Measurements and numerical values represent averages of typical plant types.

Botanical classification: *Petunia hybrida.*

PROPAGATION

Time to initiate roots: About 10 to 14 days at approximately 20° C.

Root description: Fibrous.

PLANT

Growth habit: Mounded.

Age of the plant described: Approximately 60 days.

Pot size of plant described: 13 cm.

Height: Approximately 20.

Plant spread: Approximately 35 cm.

Growth rate: Medium.

Branching characteristics: Very well branched.

Length of primary lateral branches: Approximately 25 cm.

Quantity of primary lateral branches: 8.

Characteristics of primary lateral branches:

- *Form.*—Cylindrical.
- *Diameter.*—Approximately 0.3 cm.
- *Color.*—Near RHS Yellow-Green 144A.
- *Texture.*—Pubescent.
- *Strength.*—Good.
- *Internode length.*—Average 1.5 cm.

FOLIAGE

Leaf:

- *Arrangement.*—Opposite.
- *Quantity.*—Approximately 20 per main lateral branch.
- *Average length.*—Approximately 4.0 cm.
- *Average width.*—Approximately 2.5 cm.
- *Shape of blade.*—Elliptic.
- *Apex.*—Acute.
- *Base.*—Acute.
- *Margin.*—Entire.
- *Texture of top surface.*—Velvety.
- *Texture of bottom surface.*—Light pubescence.
- *Aspect.*—90 degree angle of attachment from stem, slight downward curve of leaf blade.
- *Color.*—Young foliage upper side: Near RHS Yellow-Green 146A. Young foliage under side: Near RHS Yellow-Green 146B. Mature foliage upper side: Near RHS Yellow-Green 146A. Mature foliage under side: Near RHS Yellow-Green 146B.
- *Venation.*—Type: Pinnate. Venation color upper side: Near RHS Yellow-Green 146C. Venation color under side: Near RHS Yellow-Green 146B.
- *Petiole.*—Length: Approximately 0.5 cm. Diameter: Approximately 0.1 cm. Color: Near RHS Yellow-Green 146B. Texture: Velvety.

FLOWER

Natural flowering season: Spring, Summer, and Autumn.

Days to flowering from rooted cutting: Approximately 30 days.

Inflorescence and flower type and habit: Axillary, single flower.

Rate of flower opening: Approximately 2 to 3 days from bud to fully opened flower.

Flower longevity on plant: Approximately 3 to 6 days.

Approximate quantity of flowers per plant: Approximately 60.

Flowers persistent or self-cleaning: Self-cleaning.

Bud:

- *Shape.*—Tubular.
- *Length.*—Approximately 3.0 cm.
- *Diameter.*—Approximately 0.6 cm.
- *Color.*—Near RHS Yellow-Green 145C at proximal end and near RHS Red 46A at distal end.

Flower size:

- *Diameter.*—Approximately 3.0 cm.
- *Depth.*—Approximately 2.5 cm.
- *Flower tube diameter at distal end.*—0.8 cm.
- *Flower tube diameter at proximal end.*—0.2 cm.

Petals:

- *Width.*—Approximately 1.2 cm.
- *Length.*—Approximately 1.2 cm.
- *Quantity.*—5.
- *Texture.*—Velvety.
- *Aspect.*—Ruffled.
- *Apex.*—Blunt.
- *Margin.*—Entire.

Color:

- *When opening.*—Upper surface: Near RHS Red 46A. Lower surface: Near RHS Red 47A.
- *Fully opened.*—Upper surface: RHS Red 46 B. Lower surface: RHS Red 47 C. Flower throat (inside): RHS White 155 C. Flower throat, vein: RHS Grey-Brown 199 A. Flower tube (outside): RHS Yellow-Green 145 C. Flower tube, vein: RHS Yellow-Green 144 B.

*Fades to*.—Near RHS Red 46C.

Calyx/sepals:

*Quantity per flower*.—5.

*Shape*.—Linear.

*Length*.—Approximately 1.3 cm.

*Width*.—Approximately 0.2 cm.

*Apex*.—Rounded.

*Base*.—Cuneate.

*Margin*.—Entire.

*Texture*.—Pubescent.

*Color*.—Upper Surface: Near RHS Yellow-Green 146A. Lower Surface: Near RHS Yellow-Green 146B.

Peduncle: Not relevant.

Pedicel:

*Length*.—Approximately 2.0 cm.

*Diameter*.—Approximately 0.1 cm.

*Color*.—Near RHS Yellow-Green 146B.

*Orientation*.—Approximately 45 degrees, straight.

*Strength*.—Moderately strong and flexible.

Fragrance: None.

REPRODUCTIVE ORGANS

Stamens:

*Number*.—5.

*Filament length*.—Average 1.5 cm.

Anthers:

*Length*.—Approximately 0.1 cm.

*Shape*.—Rounded.

*Color*.—Near RHS Orange-Yellow 159B.

*Pollen*.—Near RHS Yellow 2D.

Pistil:

*Number*.—1.

*Length*.—About 2.0 cm.

*Style*.—Length: about 1.5 cm. Color: Near RHS Yellow-Green 146D.

*Stigma*.—Shape: Rounded.

*Color*.—Near RHS Yellow-Green 145B.

*Ovary color*.—Near RHS Yellow-Green 145B.

OTHER CHARACTERISTICS

Seeds and fruits:

*Quantity*.—Approximately 50 seeds in one brown, conical capsule. Seeds 0.5 mm in diameter. Color not accurately measured with R.H.S. chart.

Disease/pest resistance: Neither resistant nor susceptible to normal diseases and pests of *Petunia*.

Temperature tolerance: The new variety tolerates temperatures between approximately 5° C. to 40° C.

What is claimed is:

1. A new and distinct cultivar of *Petunia* plant named 'DLITRDFIRE' as herein illustrated and described.

* * * * *